(12) United States Patent
Schneider

(10) Patent No.: US 11,969,567 B2
(45) Date of Patent: Apr. 30, 2024

(54) BALLOON ANGIOPLASTY CATHETER COATING TO ENCOURAGE VESSEL REPAIR AND FURTHER REDUCE RESTENOSIS

(71) Applicant: SPECTRANETICS LLC, Colorado Springs, CO (US)

(72) Inventor: Blaine Schneider, Colorado Springs, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 0 days.

(21) Appl. No.: 15/354,237

(22) Filed: Nov. 17, 2016

(65) Prior Publication Data

US 2017/0136219 A1 May 18, 2017

Related U.S. Application Data

(60) Provisional application No. 62/256,845, filed on Nov. 18, 2015.

(51) Int. Cl.
*A61M 25/10* (2013.01)
*A61L 29/08* (2006.01)
(Continued)

(52) U.S. Cl.
CPC ......... *A61M 25/104* (2013.01); *A61L 29/085* (2013.01); *A61L 29/16* (2013.01); *A61B 2017/22061* (2013.01); *A61B 17/320725* (2013.01); *A61L 2300/22* (2013.01); *A61L 2300/416* (2013.01); *A61L 2300/606* (2013.01);
(Continued)

(58) Field of Classification Search
CPC ............ A61M 25/104; A61M 25/1011; A61M 2025/105; A61M 25/10; A61L 29/085; A61L 29/16; A61L 2300/22; A61L 2300/416; A61L 2300/606; A61L 2300/624; A61L 2300/12; A61L 2400/12; A61B 17/320725; A61B 2017/22061
See application file for complete search history.

(56) References Cited

U.S. PATENT DOCUMENTS 4,782,834 A * 11/1988 Maguire ............. A61M 25/104
604/103.1
6,306,166 B1 * 10/2001 Barry ...................... A61L 27/34
623/1.42
(Continued)

OTHER PUBLICATIONS

Che-Ming J. Hu, "Nanoparticle biointerfacing by platelet membrane cloaking", Oct. 1, 2015, Nature, 526 (Year: 2015).*
(Continued)

*Primary Examiner* — Tasnim Mehjabin Ahmed

(57) ABSTRACT

A method for treating a target vascular portion of a subject including: providing an angioplasty balloon system including a balloon carrying a first therapeutic agent and a second therapeutic agent on a surface of the balloon, wherein the first therapeutic agent is an anti-proliferative or anti-mitotic agent and the second therapeutic agent is a drug that aids in vascular healing on a surface of the balloon; positioning the balloon proximate the target vascular portion; expanding the balloon to engage the target vascular portion; thereby delivering at least a portion of the active agent to the target vascular portion; and withdrawing the balloon from the subject.

5 Claims, 8 Drawing Sheets

(51) Int. Cl.
*A61L 29/16* (2006.01)
*A61B 17/22* (2006.01)
*A61B 17/3207* (2006.01)

(52) U.S. Cl.
CPC ..... *A61L 2300/624* (2013.01); *A61L 2400/12* (2013.01); *A61M 25/1011* (2013.01); *A61M 2025/105* (2013.01)

(56) References Cited

U.S. PATENT DOCUMENTS

| | | | |
|---|---|---|---|
| 8,114,429 B2 | 2/2012 | Michal | |
| 8,128,951 B2 | 3/2012 | Michal | |
| 8,257,304 B2 | 9/2012 | Vreeman | |
| 8,257,722 B2 | 9/2012 | Michal | |
| 8,491,925 B2 | 7/2013 | Michal | |
| 8,563,023 B2 | 10/2013 | Michal | |
| 8,673,332 B2 | 3/2014 | Michal | |
| 8,721,667 B2 | 5/2014 | Konstantino et al. | |
| 8,734,825 B2 | 5/2014 | Michal et al. | |
| 8,740,841 B2 | 6/2014 | Vreeman | |
| 9,011,896 B2 | 4/2015 | Speck et al. | |
| 2006/0259005 A1 | 11/2006 | Konstantino | |
| 2009/0270906 A1* | 10/2009 | Hossainy | A61F 2/82 606/194 |
| 2010/0068170 A1 | 3/2010 | Michal | |
| 2010/0069879 A1* | 3/2010 | Michal | A61M 25/104 604/509 |
| 2010/0198190 A1 | 8/2010 | Michal | |
| 2012/0078228 A1 | 3/2012 | Michal | |
| 2012/0289933 A1 | 11/2012 | Michal | |
| 2013/0023817 A1 | 1/2013 | Speck et al. | |
| 2013/0046231 A1 | 2/2013 | Speck et al. | |
| 2013/0204179 A1 | 8/2013 | Konstantino et al. | |
| 2013/0338572 A1 | 12/2013 | Speck et al. | |
| 2014/0004253 A1 | 1/2014 | Ruane | |
| 2014/0023591 A1* | 1/2014 | Sen Gupta | A61K 47/48815 424/9.6 |
| 2014/0128801 A1 | 5/2014 | Speck et al. | |
| 2014/0171864 A1 | 6/2014 | Michal et al. | |
| 2014/0188036 A1 | 7/2014 | Speck et al. | |
| 2014/0221976 A1 | 8/2014 | Michal et al. | |
| 2014/0343090 A1 | 11/2014 | Michal et al. | |
| 2015/0209555 A1 | 7/2015 | Ruane et al. | |
| 2015/0216829 A1* | 8/2015 | Conte | A61K 45/06 514/560 |
| 2015/0297797 A1 | 10/2015 | Speck et al. | |

OTHER PUBLICATIONS

Pavo, N., Samaha, E., Sabdyusheva, I. et al. Coating of intravascular balloon with paclitaxel prevents constrictive remodeling of the dilated porcine femoral artery due to inhibition of intimal and media fibrosis. J Mater Sci: Mater Med 27, 131 (2016). <https://doi.org/10.1007/s10856-016-5737-y> (Year: 2016).*

Che-Ming J. Hu, et al, (Oct. 1, 2015). Nanoparticle biointerfacing by platelet membrane cloaking. Nature. 526, pp. 118-121.

Expired U.S. Appl. No. 62/098,242, filed Dec. 30, 2014. Kenneth P. Grace. Laser-induced shock waves for the treatment of vascular conditions.

Expired U.S. Appl. No. 60/680,450, filed May 11, 2005. Eitan Konstantino. Methods and systems for delivering substances into luminal walls.

Expired U.S. Appl. No. 61/665,758, filed Jun. 28, 2012. Patrick H. Ruane. Post-processing of a medical device to control morphology and mechanical properties.

* cited by examiner

FIG. 1A
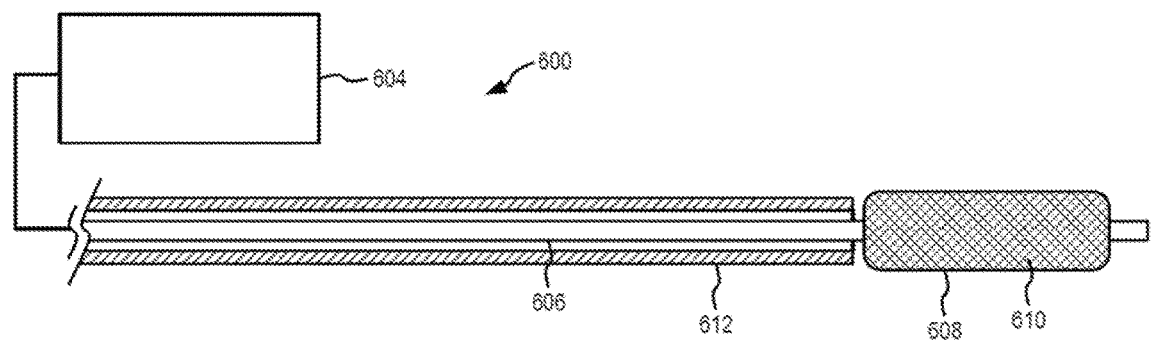
FIG. 1A'
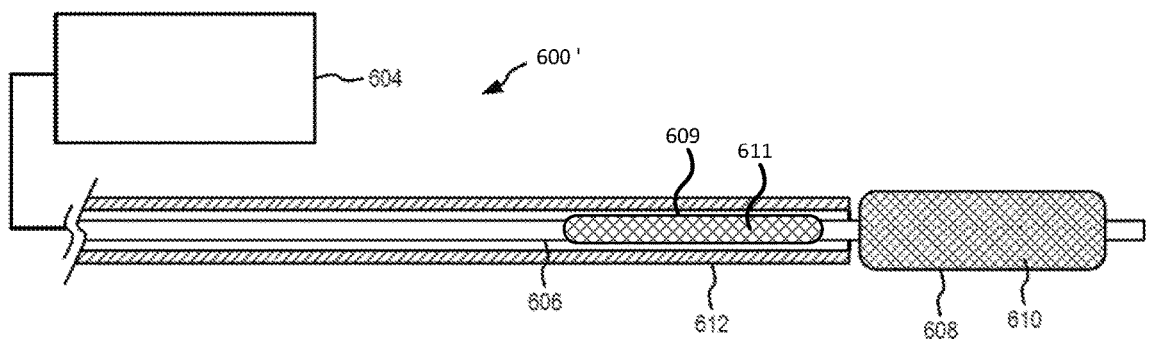
FIGS. 1A-1A'

FIG. 1B
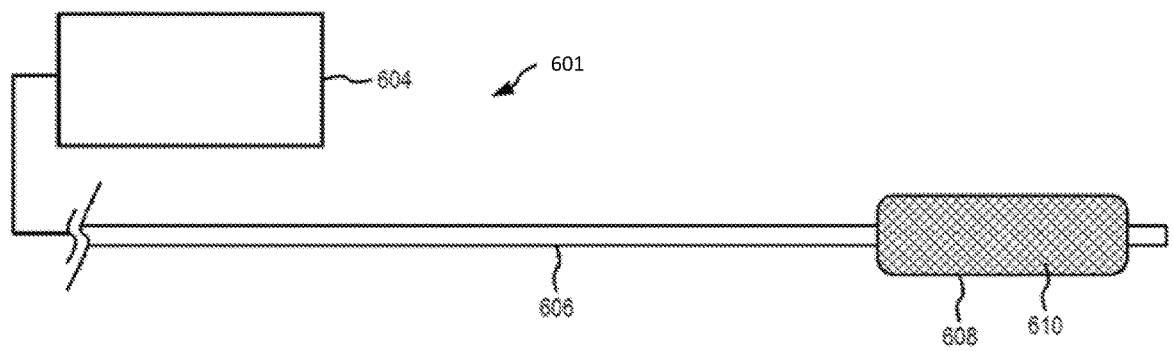
FIG. 1B'
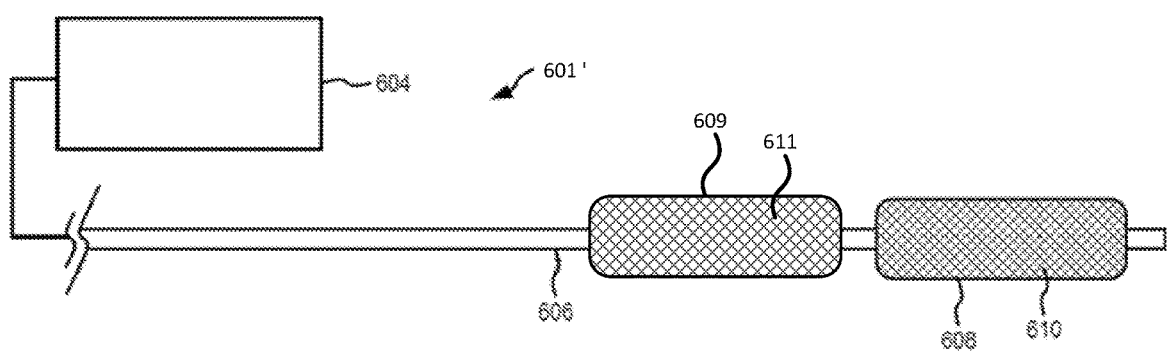
FIGS. 1B-1B'

FIG. 2A
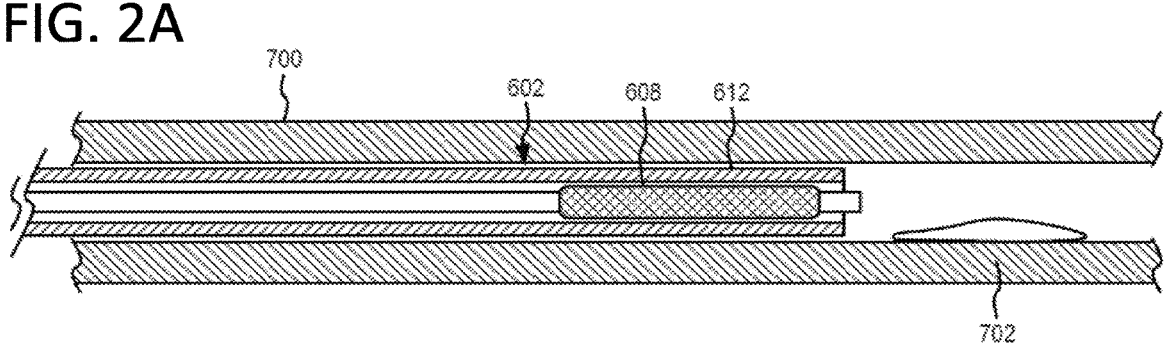
FIG. 2A'
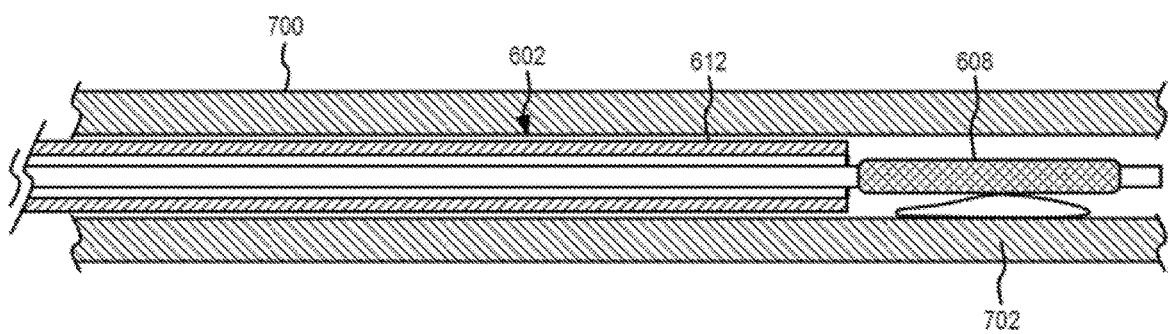
FIGS. 2A-2A'

FIG. 2B
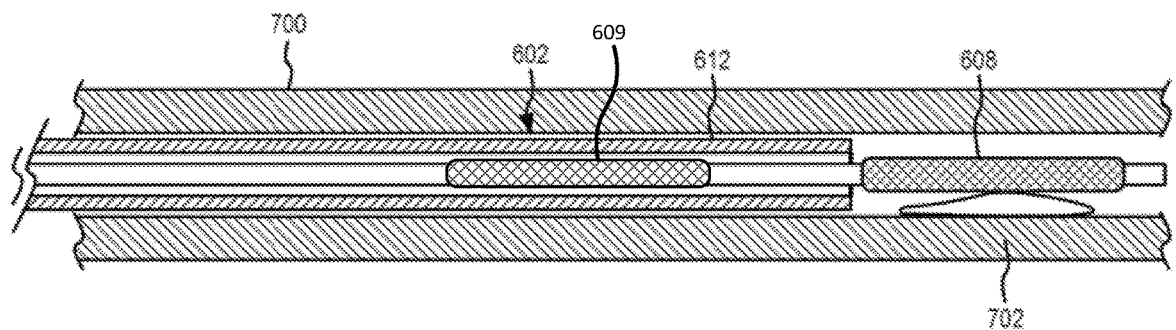
FIG. 2B'
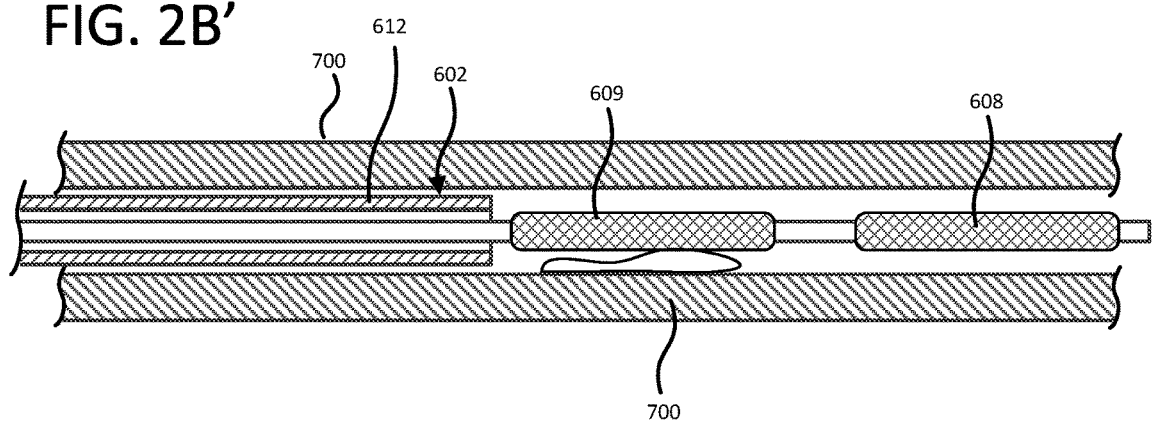
FIGS. 2B-2B'

FIG. 2C
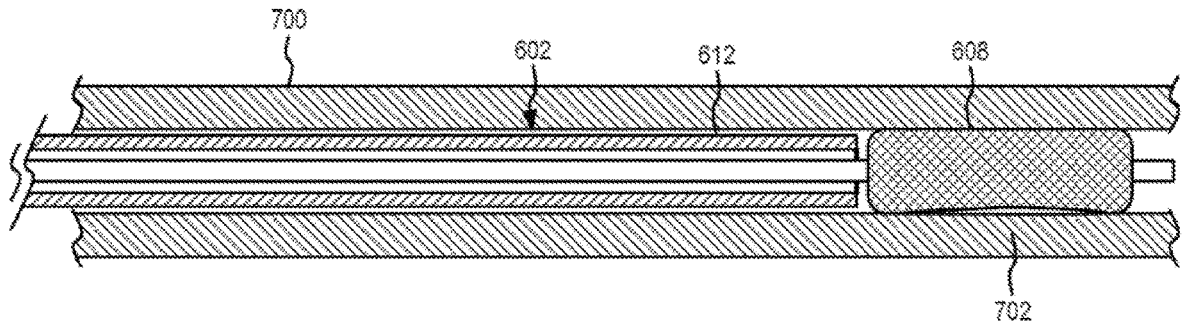
FIG. 2C'
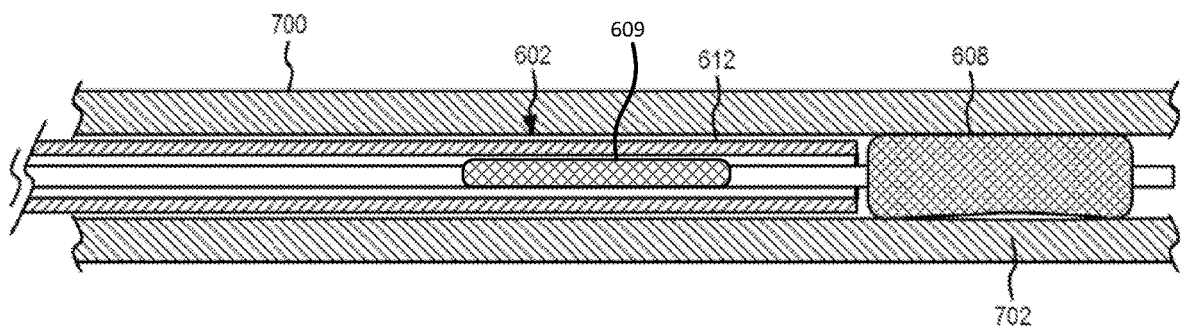
FIG. 2D
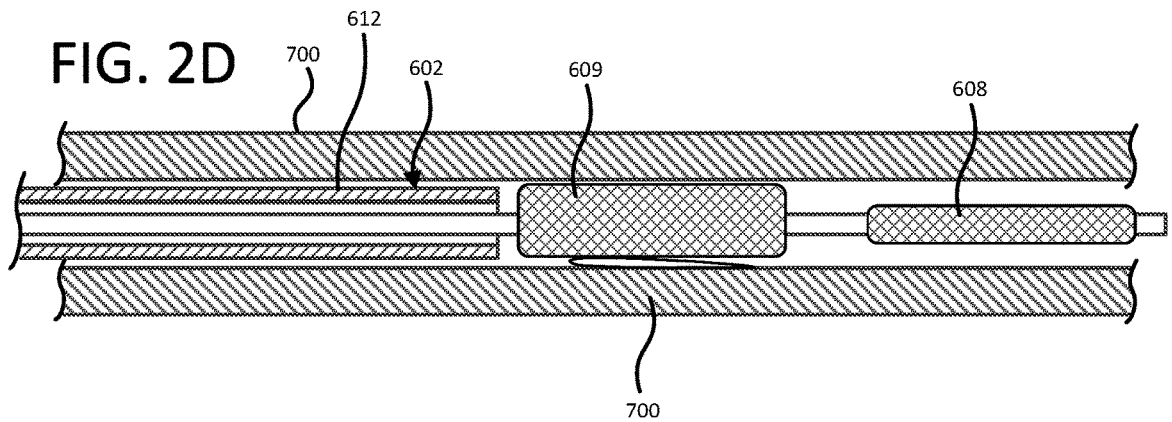
FIGS. 2C-2D

BALLOON ANGIOPLASTY CATHETER COATING TO ENCOURAGE VESSEL REPAIR AND FURTHER REDUCE RESTENOSIS

CROSS REFERENCE TO RELATED APPLICATION

This non-provisional patent application claims priority to and the benefit of U.S. Provisional Patent Application Ser. No. 62/256,845, filed Nov. 18, 2015. This application is incorporated herein by reference in its entirety for all purposes.

FIELD OF THE DISCLOSURE

The present disclosure relates generally to the use of medical devices for the treatment of vascular conditions. In particular, the present disclosure provides methods for treating vascular stenoses by delivering therapeutic agents via balloon catheters to the stenoses.

BACKGROUND

Coronary artery disease (CAD) is a common form of heart disease, affecting millions of Americans. Peripheral artery disease (PAD), also called peripheral arterial disease, is a common circulatory problem in which narrowed arteries reduce blood flow in an individual's limbs, such as arms and legs. CAD and PAD often result from a condition known as atherosclerosis, which generally manifests as the accumulation of a waxy substance on the inside of a subject's arteries. This substance, called plaque, is made of cholesterol, fatty compounds, calcium, and a blood-clotting material called fibrin. As the plaque builds up, the artery narrows, or becomes stenotic, making it more difficult for blood to flow to the heart and/or extremities.

Balloon angioplasty and other transluminal medical treatments are well-known and have been proven efficacious in the treatment of stenotic lesions at the core of CAD and PAD. In a typical angioplasty procedure, a catheter is inserted into the groin or arm of a subject and guided forward into, in the case of CAD, the coronary arteries of the heart or, in the case of PAD, into the narrowed portion of the arteries in the legs. There, blocked (partially blocked or fully blocked) arteries can be unblocked by increasing the size of the passageway within the artery with a balloon positioned at the tip of the catheter. Initially, angioplasty was performed only with balloon catheters, but technical advances have been made and improved patient outcomes have been achieved with the placement of small metallic spring-like devices called "stents" at the site of the blockage. The implanted stent serves as a scaffold that keeps the artery open. Angioplasty and stenting techniques are widely used around the world and provide an alternative option to bypass surgery for improving blood flow to the heart muscle. There are, however, limitations associated with angioplasty and stenting, one of which is called "restenosis."

Restenosis occurs when the treated vessel becomes blocked again—when the stenosis reforms within the vessel. For example, when a stent is placed in a blood vessel, new tissue grows inside the stent, covering the struts of the stent. Initially, this new tissue consists of healthy cells from the lining of the arterial wall (that is, endothelium). This is a favorable effect because development of normal lining over the stent allows blood to flow smoothly over the stented area without clotting. Later, scar tissue may form underneath the new healthy lining. However, in about 25 percent of patients, the growth of scar tissue underneath the lining of the artery may be so thick that it can obstruct the blood flow and produce another blockage. "In-stent" restenosis is typically seen 3 to 6 months after the initial procedure. Another significant limitation of the use of stents is stent thrombosis, which, although rare (occurring in only 1 percent of patients), most commonly presents as acute myocardial infarction.

In addition to angioplasty and the deployment of stents, other types of intervention for stenotic vessels include atherectomy, bypass surgery, and the use of laser ablation and mechanical cutting systems to reduce the plaque size. Treatments using various pharmacological agents have also been developed, including drug-coated balloons (DCB). Exemplary drug-coated balloons are disclosed in U.S. Pat. No. 9,011,896, the disclosures of which are hereby incorporated by reference in their entirety.

In a DCB, a drug is provided, sometimes with a coating or other substance, on an outer surface of the balloon. An exemplary drug is paclitaxel. Paclitaxel has been shown to reduce restenosis. When the balloon is inflated, the drug-coated surface is placed into contact with the passageway within the artery.

However, although the use of paclitaxel as a coating on an outer surface of a balloon can reduce restenosis, paclitaxel may also reduce or prevent vascular healing, particularly in the vascular intima, the inner layer of the vessel, where healing is desired following angioplasty. Because the vessel may not heal quickly in the presence of paclitaxel, the risk of late stent thrombosis is increased and the restenosis cascade can still be 'active'. The damage to the vessel wall that may be caused by angioplasty or stent placement, such as de-endothelialization and stretch of the vessel, may be accompanied by vessel inflammation. This inflammatory immune response typically involves the binding of platelets, fibrin, and leukocytes and the release of growth factors that stimulate migration of smooth muscle cells (SMCs) from the media into the neointima. This migration may lead to a reduction of vessel lumen area through the creation of neointimal hyperplasia, which can be a primary feature of restenosis. Additionally, the concentration of paclitaxel within the vascular wall decreases with time. If the endothelial layer is delayed in its healing, and if the paclitaxel concentration is too low to prevent SMC replication, then the restenosis cascade may be reinitiated due to the continually damaged endothelial layer, possibly leading to another inflammatory healing response.

Improvements in one or more aspects of the foregoing are desired.

SUMMARY

Given the persistence of CAD and PAD, the most efficacious means for improving therapeutic outcomes may involve combinations of therapies designed not only to reduce plaque size in the short term, but also to prevent future complications such as restenosis. These and other needs are addressed by the various aspects, embodiments, and configurations of the present disclosure.

Apparatus and methods according to the present disclosure generally relate to treating vascular stenoses (for example, scar tissue, plaque build-up, calcium deposits and other types of undesirable lesion) by using balloon angioplasty and drug delivery via drug-coated balloons.

In an exemplary embodiment, an angioplasty balloon catheter is provided. The angioplasty balloon catheter comprises an inflatable balloon coupled to the catheter, wherein the inflatable balloon comprises a balloon surface, and a coating on at least a portion of the balloon surface. The coating includes a first therapeutic agent and a second therapeutic agent. The first therapeutic agent comprises an anti-proliferative or anti-mitotic agent. The second therapeutic agent comprises a drug that aids in vascular healing.

In another exemplary embodiment, a method for treating a target vascular portion of a subject is provided. The method includes providing an angioplasty balloon system including a balloon carrying a first therapeutic agent and a second therapeutic agent on a surface of the balloon, wherein the first therapeutic agent is an anti-proliferative or anti-mitotic agent and the second therapeutic agent is a drug that aids in vascular healing on a surface of the balloon; positioning the balloon proximate the target vascular portion; expanding the balloon to engage the target vascular portion; thereby delivering at least a portion of the active agent to the target vascular portion; and withdrawing the balloon from the subject.

In a more particular embodiment of any of the above embodiments, the first therapeutic agent is a restenosis inhibitor. In an even more particular embodiment of any of the above embodiments, the first therapeutic agent is selected from the group consisting of paclitaxel, docetaxel, abraxane, sirolimus, everolimus, zotarolimus, and tranilast. In a still more particular embodiment of any of the above embodiments, the first therapeutic agent is paclitaxel.

In a more particular embodiment of any of the above embodiments, the second therapeutic agent is a selected from the class of pro-resolving mediators (PRMs). In an even more particular embodiment of any of the above embodiments, the second therapeutic agent is selected from the group consisting of: derivatives of omega-3 polyunsaturated fatty acids and omega-6 polyunsaturated fatty acids, such as resolvins, protectins, lipoxins and maresins and their therapeutically stable analogs. In a still more particular embodiment of any of the above embodiments, the second therapeutic agent is selected from the group consisting of hydroxylated derivatives of eicosapentaenoic acid (EPA) and hydroxylated derivatives of docosahexaenoic acid (DHA).

In another more particular embodiment of any of the above embodiments, the first therapeutic agent is transported to the medial layer of the target vascular portion upon inflation of the inflatable balloon and the second therapeutic agent contacts the intima of the target vascular portion upon inflation of the inflatable balloon and promotes healing of the intima of the target vascular portion.

In an exemplary embodiment, neither the first therapeutic agent nor the second therapeutic agent is provided as a polymeric nanoparticle.

In another more particular embodiment of any of the above embodiments, the second therapeutic agent is at least partially encapsulated by a polymeric nanoparticle. In a more particular embodiment, the polymeric nanoparticle is formed from poly(lactic-co-glycolic acid). In another more particular embodiment, the polymeric nanoparticle has at least one dimension measuring from 1 nm to 120 nm. In another more particular embodiment, the polymeric nanoparticle is encapsulated within a platelet membrane.

In another exemplary embodiment, the present disclosure provides an angioplasty balloon comprising a catheter, a proximal inflatable balloon coupled to the catheter, wherein the proximal inflatable balloon comprises a first balloon surface, a first coating on at least a portion of the proximal balloon surface, wherein the first coating comprises a first therapeutic agent and a second therapeutic agent, wherein the first therapeutic agent is an anti-proliferative or anti-mitotic agent and the second therapeutic agent is a drug that aids in vascular healing. The angioplasty balloon system also includes a distal inflatable balloon coupled to the catheter, wherein the distal inflatable balloon comprises a distal balloon surface, and a second coating on at least a portion of the distal balloon surface, wherein the second coating comprises a first therapeutic agent and a second therapeutic agent, wherein the first therapeutic agent is an anti-proliferative or anti-mitotic agent and the second therapeutic agent is a drug that aids in vascular healing.

In another exemplary embodiment, the present disclosure provides an angioplasty balloon comprising a catheter, a proximal inflatable balloon coupled to the catheter, wherein the proximal inflatable balloon comprises a first balloon surface, a first coating on at least a portion of the proximal balloon surface, wherein the first coating comprises a first therapeutic agent, wherein the first therapeutic agent is an anti-proliferative or anti-mitotic agent, a distal inflatable balloon coupled to the catheter, wherein the distal inflatable balloon comprises a distal balloon surface, and a second coating on at least a portion of the distal balloon surface, wherein the second coating comprises a second therapeutic agent, wherein the second therapeutic agent is a drug that aids in vascular healing.

In another exemplary embodiment, the present disclosure provides an angioplasty system comprising a first catheter, a proximal inflatable balloon coupled to the first catheter, wherein the proximal inflatable balloon comprises a first balloon surface a first coating on at least a portion of the proximal balloon surface, wherein the first coating comprises a first therapeutic agent, wherein the first therapeutic agent is an anti-proliferative or anti-mitotic agent, a second catheter, a distal inflatable balloon coupled to the second catheter, wherein the distal inflatable balloon comprises a distal balloon surface, and a second coating on at least a portion of the distal balloon surface, wherein the second coating comprises a second therapeutic agent, wherein the second therapeutic agent is a drug that aids in vascular healing.

Embodiments also include methods for treating a vascular target portion of a subject using any of the balloon catheters and balloon catheter systems of the present disclosure, including providing such a balloon catheter or balloon catheter system, positioning the distal balloon proximate the target vascular portion, expanding the distal balloon to engage the target vascular portion, thereby delivering at least a portion of the first therapeutic agent and the second therapeutic agent to the target vascular portion, positioning the proximal balloon proximate the target vascular portion, and expanding the proximal balloon to engage the target vascular portion, thereby delivering at least a portion of the first therapeutic agent and the second therapeutic agent to the target vascular portion.

In some embodiments, the method includes providing a balloon catheter or balloon catheter system, positioning the distal balloon proximate the target vascular portion, expanding the distal balloon to engage the target vascular portion, thereby delivering at least a portion of the first therapeutic agent, positioning the proximal balloon proximate the target vascular portion, and expanding the proximal balloon to engage the target vascular portion, thereby delivering at least a portion of the second therapeutic agent to the target vascular portion.

In some embodiments, the method includes providing a balloon catheter or balloon catheter system, positioning the distal balloon proximate the target vascular portion, expanding the distal balloon to engage the target vascular portion, thereby delivering at least a portion of the first therapeutic agent to the target vascular portion, positioning the proximal balloon proximate the target vascular portion, and expanding the proximal balloon to engage the target vascular portion, thereby delivering at least a portion of the second therapeutic agent to the target vascular portion.

Embodiments of any of the methods of the present disclosure can also include deflating the distal balloon deflating the proximal balloon, and withdrawing the proximal balloon and the distal balloon from the subject.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "amphiphilic" as used herein generally refers to a material that is at least partially dissolvable in aqueous solvents, such as blood in-vivo, as well as at least partially dissolvable in non-aqueous solvents, such as ethanol, methanol, and/or isopropanol.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The terms "vasculature" and "vascular" as used herein refer to any part of the circulatory system of a subject, including peripheral and non-peripheral arteries and veins. Vascular material found within the vasculature can be comprised of both biological material (for example, nucleic acids, amino acids, carbohydrates, polysaccharides, lipids and the like) and non-biological material (for example, fat deposits, fibrous tissue, calcium deposits, remnants of dead cells, cellular debris and the like).

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "balloon catheter" as used herein generally refers to the various types of angioplasty catheters which carry a balloon for performing angioplasty. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

The term "stenosis" as used herein generally refers to an abnormal narrowing in a blood vessel, the vasculature or other tubular organ or structure. There are many causes of a stenosis. One cause is atherosclerosis (also known as arteriosclerotic vascular disease), which is a specific form of arteriosclerosis in which a vasculature wall thickens as a result of invasion and accumulation of white blood cells. The thickening of the wall can lead to the formation of a thrombus within the lumen of the vasculature, whereby the thrombus may fully or partially occlude the lumen. "Restenosis" is the recurrence of stenosis after a procedure to initially treat the stenosis.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; anthelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The term "therapeutically effective amount" refers to a sufficient amount of the therapeutic agents to treat disorders, at a reasonable benefit/risk ratio applicable to any medical treatment. It will be understood, however, that the total daily usage of the therapeutic agents and compositions of embodiments of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the therapeutic agent at levels lower than required to achieve the desired therapeutic effect and to gradually increase the dosage until the desired effect is achieved.

The term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout the present disclosure is deemed to include each and every lower numerical limitation as an alternative, as if such lower numerical limitations were expressly written herein. Every minimum numerical limitation given throughout the present disclosure is deemed to include each and every higher numerical limitation as an alternative, as if such higher numerical limitations were expressly written herein. Every numerical range given throughout the present disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1A is a schematic view of an exemplary embodiment of a balloon system in accordance with the present disclosure; a balloon of a balloon catheter of the system is illustrated in an expanded configuration and a distally advanced position relative to a protective sheath;

FIG. 1A' is a schematic view of an exemplary embodiment of a balloon system in accordance with the present disclosure; a balloon of a balloon catheter of the system is illustrated in an expanded configuration and a distally advanced position relative to a protective sheath, with a proximally positioned second balloon in an unexpanded configuration within the protective sheath;

FIG. 1B is a schematic view of another exemplary embodiment of a balloon system in accordance with the present disclosure without a protective sheath;

FIG. 1B' is a schematic view of another exemplary embodiment of a balloon system in accordance with the present disclosure without a protective sheath;

FIG. 2A is an elevation longitudinal section view of the balloon catheter of FIG. 1A longitudinally offset from a target to be treated; the balloon is in an unexpanded configuration and a proximally retracted position within the protective sheath;

FIG. 2A' is an elevation longitudinal section view of the balloon catheter of FIG. 1A; the balloon is in a distally advanced position relative to the protective sheath and is longitudinally aligned with the target and radially offset from the target;

FIG. 2B is an elevation longitudinal section view of the balloon catheter system of FIG. 1A, including a proximal balloon and a distal balloon; the distal balloon is in a distally advanced position relative to the protective sheath and the proximal balloon, and is longitudinally aligned with the target and radially offset from the target;

FIG. 2B' is an elevation longitudinal section view of the balloon catheter system of FIG. 1A', including a proximal balloon and a distal balloon; both the proximal balloon and the distal balloon are in unexpanded configurations and in a distally advanced position relative to the protective sheath, with the proximal balloon longitudinally aligned with the target and radially offset from the target;

FIG. 2C is an elevation longitudinal section view of the balloon catheter of FIG. 1A; the balloon is in the distally advanced position relative to the protective sheath and is longitudinally aligned with the target and radially expanded to engage the target;

FIG. 2C' is an elevation longitudinal section view of the balloon catheter system of FIG. 1A, including a proximal balloon and a distal balloon; the distal balloon is in the distally advanced position relative to the protective sheath and the proximal balloon, and is longitudinally aligned with the target and radially expanded to engage the target;

FIG. 2D is an elevation longitudinal section view of the balloon catheter system of FIG. 1A', including a proximal balloon and a distal balloon; both the proximal balloon and the distal balloon are in a distally advanced position relative to the protective sheath, with the proximal balloon longitudinally aligned with the target and radially expanded to engage the target;

DETAILED DESCRIPTION

Figure 1C:
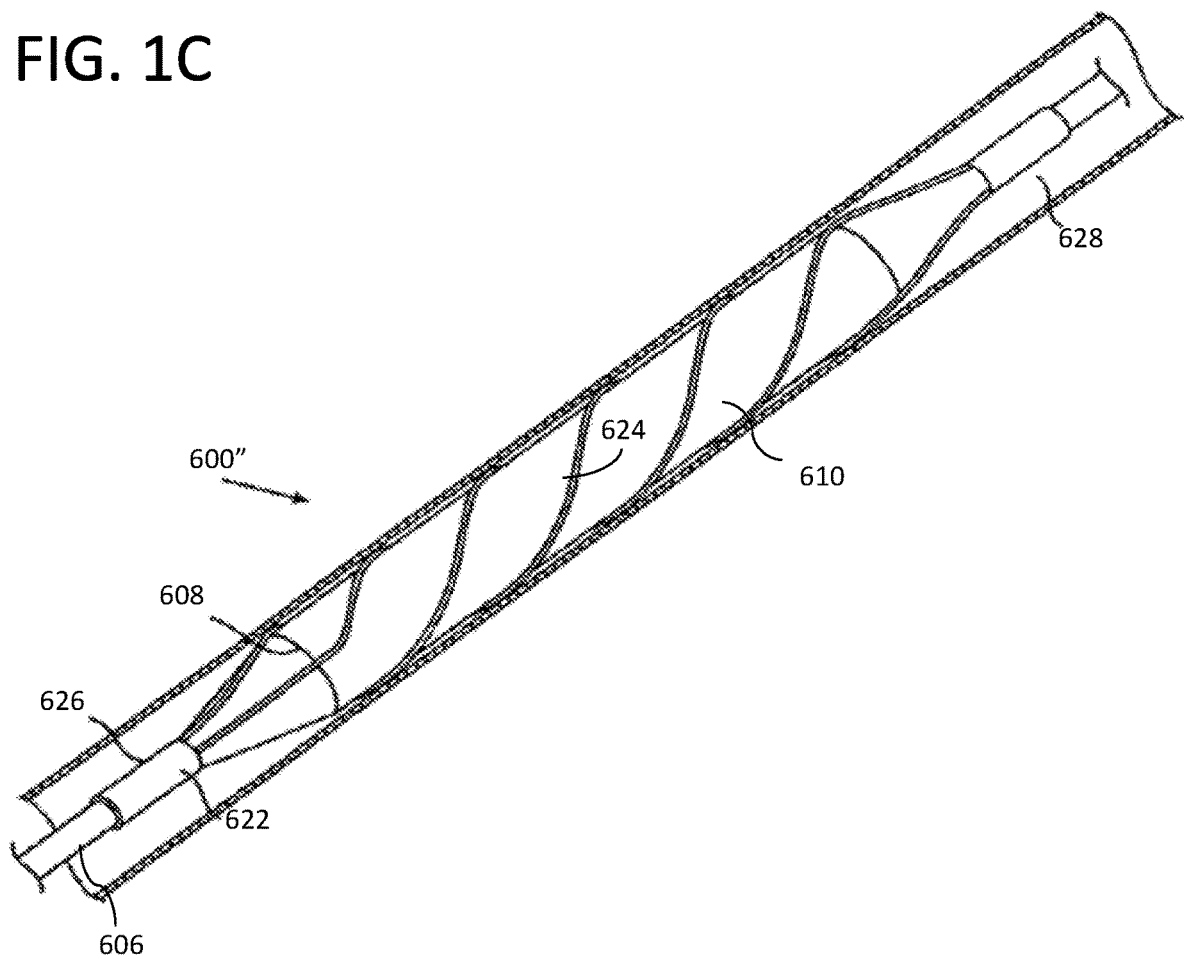
FIG. 1C illustrates an exemplary embodiment of a scoring balloon system in accordance with the present disclosure.
Figure 3:
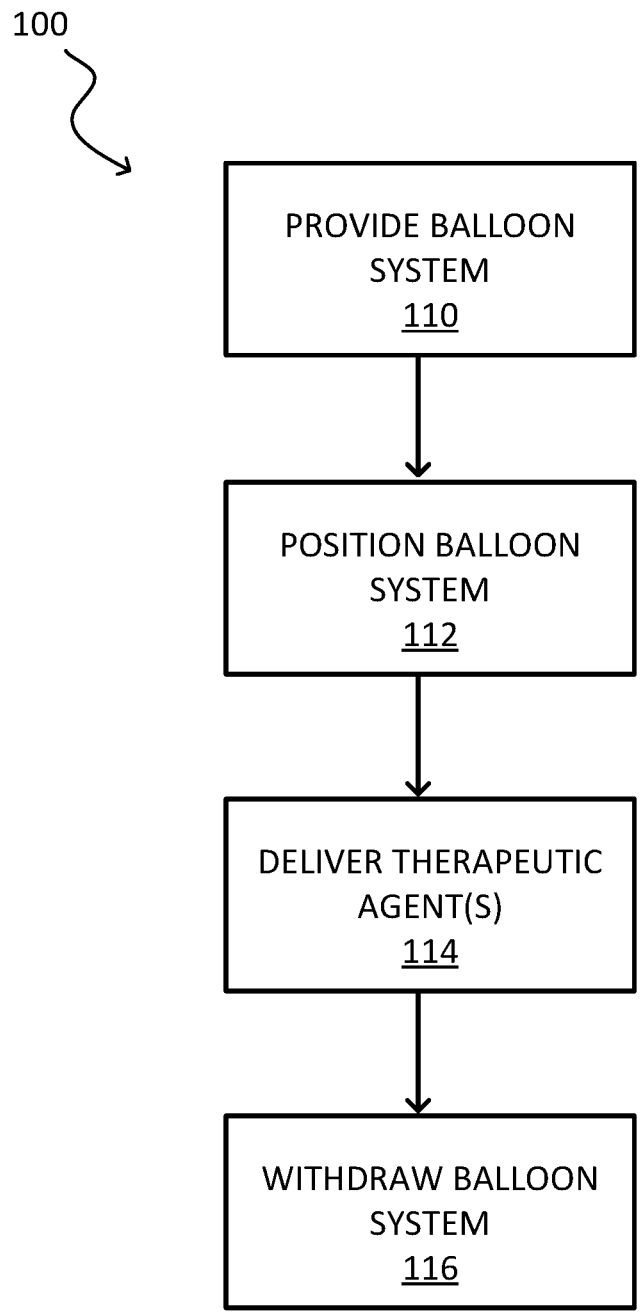
FIG. 3 is a flow diagram of an exemplary method for treating vascular stenosis via a drug-coated balloon in accordance with the present disclosure.

Methods according to the present disclosure generally relate to treating vascular stenoses (for example, scar tissue, plaque build-up, calcium deposits and other types of undesirable lesion) by using drug delivery via a balloon system. Generally and in some embodiments, the balloon system includes a drug-coated balloon (DCB) catheter, which is described in more detail below. The DCB catheter is inserted into and delivers therapeutic agents to the vasculature of a subject. In some embodiments, the balloon system also includes an inflation fluid source that delivers an inflation fluid to the DCB catheter to cause the balloon of the DCB catheter to inflate or expand and, in some embodiments, deliver the therapeutic agent(s) to the vasculature. In some embodiments, the balloon system can include an inflation fluid source that comprises a therapeutic agent, which can be delivered to the vasculature through pores in an inflated balloon (e.g., weeping balloon system).

An example of a DCB catheter includes the Stellarex™ drug coated angioplasty balloon (DCB) platform is designed to treat peripheral arterial disease. The Stellarex™ DCB platform uses EnduraCoat™ (excipient) technology, a durable, uniform coating designed to prevent drug loss during transit and facilitate controlled, efficient drug delivery to the treatment site. The Stellarex™ DCB platform received CE mark to be marketed in the European Union in December 2014. At the time of filing this application, the Stellarex™ DCB platform is not approved in the United States.

Other examples of DCB catheters in accordance with the present disclosure include those available from Lutonix, Inc. of New Hope, Minnesota under the tradename Lutonix®, such as the Lutonix® 014 catheter and those available from Medtronic PLC of Fridley, Minnesota under the tradename IN.PACT®. Further examples of DCB catheters, therapeutic agents, and balloon coatings including therapeutic agents in accordance with the present disclosure include those disclosed in U.S. Pat. Nos. 8,114,429; 8,128,951; 8,257,304; 8,257,722; 8,491,925; 8,563,023; 8,673,332; 8,721,667; 8,734,825, 8,740,841; 9,011,896; U.S. patent application Ser. Nos. 62/098,242; 13/628,608; 13/707,401; 11/411,635; 60/680,450; 13/310,320; 12/712,134; 12/558,420; 12/210,344; 14/149,862; 13/560,538; 13/926,515; 61/665,758; 13/628,627; 13/975,209; 13/975,220; 13/975,228; 14/032,336; 14/162,900; 14/254,160; 14/731,715; the entireties of which are incorporated by reference herein for all purposes.

Referring now to FIG. 1A, an exemplary embodiment of a balloon system 600 in accordance with the present disclosure is illustrated. The balloon system 600 includes a DCB catheter 602 that receives inflation fluid from an inflation fluid source 604. The DCB catheter 602 includes a tubular element 606 that carries a drug-coated expandable element or balloon 608. The tubular element 606 includes an inflation lumen (not illustrated) that receives inflation fluid from the inflation fluid source 604 and delivers the inflation fluid to the balloon 608 to inflate the balloon 608. In some embodiments, the tubular element 606 also includes a guidewire lumen (not illustrated) for receiving a guidewire (not illustrated) to guide the DCB catheter 602 to the target. The balloon 608 carries a coating 610 that includes a first therapeutic agent and a second therapeutic agent, as described in more detail below.

As shown in FIG. 1A, in some embodiments, the DCB catheter 602 further includes a protective sheath 612 that is translatable relative to the tubular element 606 and the balloon 608. The protective sheath 612 initially surrounds the unexpanded balloon 608 to prevent the coating 610 from prematurely dissolving when the DCB catheter 602 is inserted into the vasculature of the subject.

Referring now to FIG. 1A', an exemplary embodiment of a balloon system 600' in accordance with the present disclosure is illustrated. The balloon system 600' includes a DCB catheter 602 that receives inflation fluid from an inflation fluid source 604. The DCB catheter 602 includes a tubular element 606 that carries a drug-coated expandable element or balloon 608. The tubular element 606 includes an inflation lumen (not illustrated) that receives inflation fluid from the inflation fluid source 604 and delivers the inflation fluid to the balloon 608 to inflate the balloon 608. In some embodiments, the tubular element 606 also includes a guidewire lumen (not illustrated) for receiving a guidewire (not illustrated) to guide the DCB catheter 602 to the target. The balloon 608 carries a coating 610 that includes a first therapeutic agent and a second therapeutic agent, as described in more detail below.

The balloon system 600' can also include a second, proximally positioned balloon 609 that carries a coating 611 that can include the first and second therapeutic agents applied to the distal balloon 608, or the coating 611 can include a third therapeutic agent and a fourth therapeutic agent that have not been applied to the distal balloon 608. Various other combinations of these therapeutic agents can be applied to the distal balloon 608 and the proximal balloon 609, as would be recognized by one of ordinary skill in the art based on the present disclosure.

As shown in FIG. 1A', in some embodiments, the DCB catheter 602 further includes a protective sheath 612 that is translatable relative to the tubular element 606 and the balloon 608. The protective sheath 612 initially surrounds the unexpanded distal balloon 608 and/or the unexpanded proximal balloon 609 to prevent the coating 610 from prematurely dissolving when the DCB catheter 602 is inserted into the vasculature of the subject. Additionally, as shown in FIG. 1A', the distal balloon 608 and the proximal balloon 609 can be expanded and unexpanded independently. For example, the distal balloon 608 is in an expanded configuration outside of protective sheath 612, while the proximal balloon 609 is in an unexpanded configuration within the protective sheath 612.

Referring next to FIG. 1B, another exemplary balloon system 601 is illustrated. Balloon system 601 is similar to balloon system 600 in FIG. 1A, and similar parts are indicated by similar part numbers. As shown in FIG. 1B, exemplary balloon system 601 does not include a protective sheath 612. In some more particular embodiments, an excipient, coating, or other suitable material is placed over at least a portion of the surface of balloon 608 to prevent all, most, or a substantial portion of the coating 610 from prematurely dissolving when the DCB catheter 602 is inserted into the vasculature of the subject.

Referring next to FIG. 1B', another exemplary balloon system 601' is illustrated. Balloon system 601' is similar to balloon system 600' (FIG. 1A'), and similar parts are indicated by similar part numbers. As shown in FIG. 1B', exemplary balloon system 601' does not include a protective sheath 612. In some more particular embodiments, an excipient, coating, or other suitable material is placed over at least a portion of the surface of balloon 608 to prevent all, most, or a substantial portion of the coating 610 from prematurely dissolving when the DCB catheter 602 is inserted into the vasculature of the subject. Additionally, balloon system 601' can include a second balloon 609 having an excipient, coating or other suitable material 611 is applied over at least a portion of the surface of balloon 609 to prevent all, most, or a substantial portion of the excipient or coating 611 from prematurely dissolving when the DCB catheter 602 is inserted into the vasculature of the subject. The second balloon 609 can be located proximal to the first balloon (as shown in FIG. 1B'), or distal to the first balloon. In some embodiments, different therapeutic agents can be paired with the same or different excipient or coating 610, 611, depending on the chemical characteristics of the therapeutic agents, as would be recognized by one of skill in the art based on the present disclosure.

Another exemplary type of catheter system 600" that can incorporate the coating 610 of the present disclosure, which includes a first therapeutic agent and a second therapeutic agent, as described in more detail below, is a scoring balloon catheter, such as the AngioSculpt™ scoring balloon catheter, which is currently produced (without the drug coating) by AngioScore, Inc. of Colorado Springs, Colorado AngioScore, Inc. is the applicant of the present patent application. A depiction of an example of a scoring balloon is illustrated if FIG. 1C. Balloon system 600" is similar to balloon systems 600 and 600', and similar parts are indicated by similar part numbers. As shown in FIG. 1C, exemplary balloon system 600" includes an expandable, nonimplantable scoring structure 622 surrounding the balloon 608. Nonimplantable scoring structure 622 illustratively includes a plurality of wires 624 in a helical pattern around balloon 608. The scoring structure 622 may be attached to balloon system 600" with proximal collar 626 and distal collar 628. In one embodiment, the scoring structure 622 expands around the balloon 608 upon inflation of the balloon 608, scoring a luminal surface of the blood vessel. And upon deflation of the balloon 608, the scoring structure 622 retracts. In some more particular embodiments, an excipient, coating, or other suitable material is placed over at least a portion of the surface of balloon 608 to prevent all, most, or a substantial portion of the coating 610 from prematurely dissolving when the DCB catheter 602 is inserted into the vasculature of the subject.

Another exemplary type of catheter system (not shown) that can incorporate the coating of the present disclosure, which includes a first therapeutic agent and a second therapeutic agent, as described in more detail below, is the Chocolate™ balloon catheter, which is currently produced by QT Vascular Ltd. of Singapore and/or by TriReme Medical, LLC of Pleasanton, California Referring next to FIGS. 2A-2C and FIG. 3, an exemplary method 100 for treatment of vascular stenosis by drug delivery via drug-coated balloons is provided. As shown in block 110 of FIG. 3, a balloon system is provided. In one exemplary embodiment, the balloon system is balloon system 600 of FIG. 1A. In another exemplary embodiment, the balloon system is balloon system 600' of FIG. 1B. In another exemplary embodiment, the balloon system is balloon system 600" of FIG. 1C.

In block 112, the balloon systems of the present disclosure can be positioned in appropriate positions for delivering the therapeutic agent(s) to the vasculature of the subject, as shown in FIGS. 2A and 2A'. In some embodiments, positioning the balloon systems in appropriate positions includes (1) as illustrated in FIG. 2A, positioning the DCB catheter 602 in the vasculature 700 of the subject such that the catheter 602 is longitudinally offset (that is, offset in a longitudinal direction of the catheter 602) from the target 702 to be treated; the balloon 608 may be in an unexpanded configuration, and if the balloon system includes a protective sheath 612, the balloon 608 may be in a proximally retracted position within the protective sheath 612; (2) as illustrated in FIG. 2A', translating the balloon 608 to a distally advanced position relative to the protective sheath 612 such that the balloon 608 is longitudinally aligned with the target 702 and radially offset (that is, offset in a radial direction of the catheter 602) from the target 702; and (3) as illustrated in FIGS. 2C-2D, expanding the balloon 608 in the radial direction to contact the target 702. If the balloon system does not include a protective sheath 612, the balloon 608 is longitudinally aligned with the target 702 and radially offset (that is, offset in a radial direction of the catheter 602) from the target 702; and upon delivery of the inflation fluid to the balloon 608, the balloon 608 inflates and is expands in the radial direction to contact the target 702. In some embodiments, the inflation fluid source 604 delivers inflation fluid to the balloon 608 to expand the balloon 608. In some embodiments, as illustrated in FIGS. 2B and 2B', balloon systems can include a second balloon 609. The second balloon 609 can be located proximal to the first balloon, or distal to the first balloon. Each balloon can be inflated or deflated independently (as shown in FIGS. 2C' and 2D) as the system is advanced through a subject's vasculature during treatment. In some ways, the inclusion of two balloons can eliminate the need to fully remove and then reinsert a DCB catheter to deliver, for example, different therapeutic agents, in a given medical procedure.

At block 114, the balloon 608 delivers the first and second therapeutic agents to the target 702. The target may include an occlusion and/or a lesion within the vasculature. In some embodiments, the balloon 608 delivers the first and second therapeutic agents to the target 702 by the balloon 608 contacting the blood of the subject, thereby dissolving the coating 610, and/or expanding the balloon 608 to contact the target 702.

Figure 4:
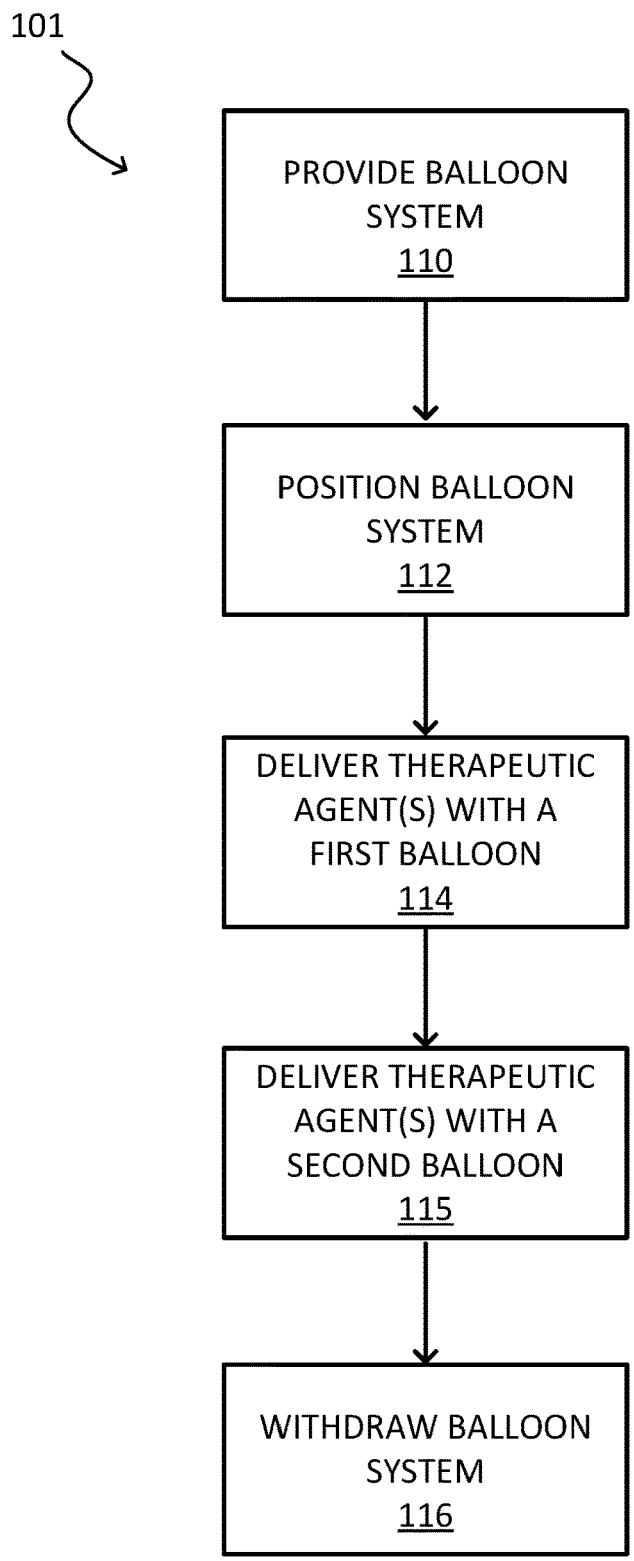
FIG. 4 is a flow diagram of an exemplary method for treating vascular stenosis via multiple drug-coated balloons in accordance with the present disclosure.

In some embodiments, such as at block 115 in FIG. 4, balloon 608 delivers a first therapeutic agent and balloon 609 delivers a second administration of the first therapeutic agent, or balloon 609 delivers a different second therapeutic agent than that delivered by balloon 608 to the target 702. The target 702 may include an occlusion and/or a lesion within the vasculature. In some embodiments, the balloons 608 and 609 deliver first and second therapeutic agents to the target 702 by contacting the blood of the subject, thereby dissolving the coatings 610 and 611 on balloons 608 and 609, respectively, and/or by expanding balloons 608 and 609 to contact the target 702. Balloons 608 and 609 can be inflated and deflated independently to deliver therapeutic agent(s).

The method concludes by withdrawing the balloon system from the subject, as shown at block 116. In some embodiments, withdrawing the balloon system from the subject includes removing the DCB catheter 602 from the vasculature 700 of the subject.

In one exemplary embodiment, the first therapeutic agent comprises an anti-proliferative or anti-mitotic agent. Exemplary anti-proliferative or anti-mitotic agents include natural products such as vinca alkaloids (i.e. vinblastine, vincristine, and vinorelbine), paclitaxel, epipodophyllotoxins (i.e. etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine);

In one exemplary embodiment, the first therapeutic agent comprises a restenosis inhibitor. Exemplary restenosis inhibitors include: paclitaxel, docetaxel, abraxane, sirolimus, everolimus, zotarolimus, and tranilast In an even more particular embodiment, the first therapeutic agent is paclitaxel.

In one exemplary embodiment, the second therapeutic agent comprises a drug that aids in vascular healing. Exemplary second therapeutic agents include PRMs, such as derivatives of omega-3 polyunsaturated fatty acids and omega-6 polyunsaturated fatty acids, such as resolvins, protectins, lipoxins and maresins and their therapeutically stable analogs. Additional exemplary PRMs are disclosed in International Patent Publication WO 2014/039964, entitled COMPOUNDS AND METHODS FOR MODULATING VASCULAR INJURY, the entire contents of which are hereby incorporated by reference in their entirety. In an even more particular embodiment, the second therapeutic agent is selected from the group consisting of: derivatives of omega-3 polyunsaturated fatty acids and omega-6 polyunsaturated fatty acids, such as resolvins, protectins, lipoxins and maresins and their therapeutically stable analogs. In a still more particular embodiment, the second therapeutic agent is selected from the group consisting of hydroxylated derivatives of eicosapentaenoic acid (EPA) and hydroxylated derivatives of docosahexaenoic acid (DHA).

In one exemplary embodiment, the first therapeutic agent is taken up into the medial layer of the vascular tissue, while the second therapeutic agent remains in contact with the intimal surface of the vascular tissue. Without wishing to be held to any particular theory, it is believed that the first therapeutic agent will inhibit restenosis, while the second therapeutic agent will promote healing of the intima, allowing for both immediate and long-term inhibition of restenosis.

In one exemplary embodiment, the first therapeutic agent and the second therapeutic agent are applied directly to the surface of the balloon.

In one exemplary embodiment, neither the first therapeutic agent nor the second therapeutic agent is provided as a polymeric nanoparticle.

In one exemplary embodiment, the second therapeutic agent is provided as a polymeric nanoparticle. The second therapeutic agent is at least partially encapsulated by the polymeric nanoparticle. Exemplary polymeric nanoparticles are formed from poly(lactic-co-glycolic acid) (PLGA). In a more particular embodiment, the polymeric nanoparticles have at least one dimension measuring 100 nm or less. In an even more particular embodiment, each particle has at least one dimension as little as 1 nm, 5 nm, 10 nm, 25 nm, as great as 50 nm, 75 nm, 100 nm, 120 nm, or within any range defined between any two of the foregoing values, such as 1 nm to 120 nm or 10 nm to 100 nm.

In a more particular embodiment, the polymeric nanoparticles containing the second therapeutic agent are shielded within a platelet membrane. Exemplary methods of making such platelet-membrane coated polymeric nanoparticles (PNPs) are provided in Che-Ming J. Hu, et al., "Nanoparticle biointerfacing by platelet membrane cloaking," *Nature*, 526, pp. 118-121, Oct. 1, 2015, the disclosures of which are attached as an Appendix and hereby incorporated by reference in their entirety. The platelet-membrane coated polymeric nanoparticles are reported to have platelet-mimicking properties including selective adhesion to damaged vascular tissue. Without wishing to be held to any particular theory, it is believed that adhering the nanoparticles containing the second therapeutic agent to the damaged vascular tissue will further aid in healing of the vasculature.

In one exemplary embodiment, additional therapeutic agents may be provided. Exemplary additional therapeutic agents include:

(1) antiproliferative and antimitotic agents such as natural products such as vinca alkaloids (i.e. vinblastine, vincristine, and vinorelbine), paclitaxel, epipodophyllotoxins (i.e. etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine);

(2) antiplatelet agents such as G(GP) inhibitors and vitronectin receptor antagonists;

(3) alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC);

(4) antiproliferative and antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine});

(5) platinum coordination complexes such as cisplatin, carboplatin, procarbazine, hydroxyurea, mitotane, and aminoglutethimide;

(6) hormones (e.g. estrogen);

(7) anticoagulants (heparin, synthetic heparin salts and other inhibitors of thrombin);

(8) fibrinolytic agents (such as tissue plasminogen activator, streptokinase and urokinase), aspirin, dipyridamole, ticlopidine, clopidogrel, abciximab;

(9) antimigratory agents;

(10) antisecretory agents (breveldin);

(11) anti-inflammatory agents, such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen;

(12) indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate);

(13) immunosuppressive agents such as cyclosporine, tacrolimus (FK-506), sirolimus (rapamycin), azathioprine, mycophenolate, mofetil;

(14) angiogenic agents such as vascular endothelial growth factor (VEGF), fibroblast growth factor (FGF);

(15) angiotensin receptor blockers;

(16) nitric oxide donors;

(17) anti-sense oligionucleotides and combinations thereof;

(18) cell cycle inhibitors, mTOR inhibitors, and growth factor receptor signal transduction kinase inhibitors;

(19) retenoids;

(20) cyclin/CDK inhibitors;

(21) HMG co-enzyme reductase inhibitors (statins); and

(22) protease inhibitors.

Additional therapeutic agents in accordance with the present disclosure can be chosen based upon functional characteristics, including, but not necessarily limited to, the ability to inhibit restenosis, mitosis or cellular proliferation. In one exemplary embodiment, For example, a therapeutic agent can be a taxane, including paclitaxel, docetaxel, protaxel, DHA-paclitaxel, PG-paclitaxel, docosahexaenoic acid (DHA), or any combinations or derivatives thereof capable of inhibiting mitosis or cellular proliferation. In some cases, the presence of a mitotic inhibitor prevents restenosis that may occur in the absence of the inhibitor. Other examples of therapeutic agents include rapamycin (for example, sirolimus) or a derivative of rapamycin (for example, everolimus), or any combinations or derivatives thereof. Additionally or alternatively, specific inhibitors of neovascularization such as thalidomide, statins such as atorvastatin, cerivastatin, fluvastatin, or anti-inflammatory drugs like corticoids or lipophilic derivatives of corticoids such as betamethasone dipropionate or dexa-methasone-21-palmitate are examples of oxitherapeutic agents that can be used in accordance with the present disclosure. In some cases, the therapeutic agent is stable against oxidative degradation, or oxidation insensitive. Various therapeutic agents may be applied or combined if different pharmacological actions are required or efficacy or tolerance is to be improved.

In some exemplary embodiments, the first and second therapeutic agents are dispersed throughout a polymer matrix. The polymer coating may include additional components such as a plasticizer and/or wax. The first and second therapeutic agents can be either water-soluble or water-insoluble. The polymer matrix may be complexed with iodine, or non-covalently bound iodine may be dispersed throughout the polymer matrix. In some embodiments, the polymer matrix is a non-ionic thermoplastic polymer or co-polymer. In some embodiments, the amphiphilic polymer is hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive double bond containing monomers such as styrene, acrylic acid, vinyl acetate or vinyl caprolactam. PVP and HPC exhibit higher solubility rates in aqueous solvents than PEG. Molecular weight of the polymers may also factor into solubility rates. In some embodiments, the PEG has as molecular weight of 1.5 kD to 50 kD. Co-polymers can be block or random.

Coatings in accordance with the present disclosure include an amphiphilic polymer coating that includes one or more therapeutic agents and one or more amphiphilic polymers or co-polymers. The amphiphilic polymer coating may include additional components such as a plasticizer and/or wax. The first and second therapeutic agents can be either water-soluble or water-insoluble. Hydration of the amphiphilic polymer coating occurs immediately when exposed to aqueous fluids, such as blood in vivo, causing the amphiphilic polymer coating to dissolve and the therapeutic agent to release into tissue of the vasculature of the subject. Thus, the amphiphilic polymer coating is bioerodible in the sense that it is removable by bodily fluids, and non-durable. In some embodiments, the amphiphilic polymer or co-polymer is a non-ionic thermoplastic polymer or co-polymer. In some embodiments, the amphiphilic polymer is hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive double bond containing monomers such as styrene, acrylic acid, vinyl acetate or vinyl caprolactam. PVP and HPC exhibit higher solubility rates in aqueous solvents than PEG. Molecular weight of the polymers may also factor into solubility rates. In some embodiments, the PEG has as molecular weight of 1.5 kD to 50 kD. In some embodiments, the coating includes paclitaxel in PEG complexed with iodine in a polymer matrix, or non-covalently bound iodine may be dispersed throughout the polymer matrix. The PEG has a number average molecular weight, Mn, of about 8 kD. The amphiphilic polymer may also be a poly(hydroxyethyl methacrylic) acid, also known as poly(HEMA). In some embodiments, the poly(HEMA) has a number average molecular weight, Mn, below approximately 8 kD. In some embodiments, the poly(HEMA) has a number average molecular weight, Mn, of approximately 7 kD. In some embodiments, the amphiphilic polymer may be a co-polymer of HEMA with a monomer such as glycidyl methacrylate (GMA) or acrylic acid. Co-polymers can be block or random.

Coatings in accordance with the present disclosure may include various adjuvants and excipients to enhance efficacy or delivery of the first and second therapeutic agents. For example, the first and second therapeutic agents can be combined with lipophilic antioxidant such as nordihydroguaiaretic acid, resveratrol, propyl gallate, hydroxytoluene, butylated hydroxyanisole, and ascorbyl palmitate to enhance the adhesion of the therapeutic to the balloon 608. In some embodiments, the combination of a therapeutic agent such as paclitaxel and a lipophilic antioxidant such as nordihydroguaiaretic acid can be applied to the balloon 608 without the need for additional polymers.

Coatings in accordance with the present disclosure may be applied to balloons by using a variety of processes. For example, coatings may be applied to balloons using an automated coating apparatus, by dipping, sputtering, and hand coating.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A method for treating a target vascular portion of a subject with an angioplasty balloon system including an angioplasty balloon, wherein a surface of the angioplasty balloon carries both:
   an amphiphilic polymer and paclitaxel directly on a portion of a surface of the angioplasty balloon, and pro-resolving mediators directly on the portion of the surface of the angioplasty balloon, wherein the pro-resolving mediators are at least partially encapsulated by a polymeric nanoparticle, the method comprising:

positioning the angioplasty balloon proximate the target vascular portion;

expanding the angioplasty balloon to engage the target vascular portion with the portion of the surface of the angioplasty balloon carrying the paclitaxel and the pro-resolving mediators contacting the target vascular portion, thereby simultaneously delivering both the paclitaxel and the pro-resolving mediators to the target vascular portion upon contact of the portion of the surface of the angioplasty balloon with the target vascular portion, wherein the paclitaxel is taken up into a medial layer of vascular tissue at the target vascular portion, while the pro-resolving mediators remain in contact with an intimal surface of the vascular tissue;

subsequently deflating the angioplasty balloon; and subsequent to the deflating, withdrawing the angioplasty balloon system from the subject.

2. The method of claim 1, wherein the paclitaxel is a restenosis inhibitor.

3. The method of claim 1, wherein the pro-resolving mediators are selected from the group consisting of derivatives of omega-3 polyunsaturated fatty acids and omega-6 polyunsaturated fatty acids.

4. The method of claim 1 wherein the angioplasty balloon system further comprises a fluid delivery system coupled to expand the angioplasty balloon by supplying a fluid via a delivery lumen.

5. The method of claim 1, wherein the polymeric nanoparticle is encapsulated within a platelet membrane.

* * * * *